United States Patent [19]

Munshi

[11] 4,427,681
[45] Jan. 24, 1984

[54] THIXOTROPIC COMPOSITIONS EASILY CONVERTIBLE TO POURABLE LIQUIDS

[75] Inventor: Mayank V. Munshi, E. Norwalk, Conn.

[73] Assignee: Richardson-Vicks, Inc., Phillipsburg, N.J.

[21] Appl. No.: 419,022

[22] Filed: Sep. 16, 1982

[51] Int. Cl.$^3$ .................... A61K 31/485; A61K 47/00
[52] U.S. Cl. .................................... 424/260; 424/263; 424/324; 424/330; 424/341; 424/362; 252/315.3
[58] Field of Search .............................. 424/362, 260; 252/315.3

[56] References Cited

U.S. PATENT DOCUMENTS 3,134,720  5/1964  Green et al. .................... 424/362 X
3,927,205  12/1975  Ohno et al. ............................ 428/80
4,284,649  8/1981  Wiczer ................................ 424/362

*Primary Examiner*—Leonard Schenkman
*Attorney, Agent, or Firm*—George W. Rauchfuss, Jr.

[57] ABSTRACT

Compositions employing titanium dioxide as an opacifying agent and which are thixotropic gels easily convertible to pourable liquids with moderate shaking are provided by employing Avicel ® RC-591 as the suspending agent for the composition.

16 Claims, No Drawings

THIXOTROPIC COMPOSITIONS EASILY CONVERTIBLE TO POURABLE LIQUIDS

FIELD OF THE INVENTION

This invention relates to thixotropic compositions which are easily convertible to pourable liquids and more particularly to thixotropic compositions containing titanium dioxide which are easily convertible to pourable liquids and which are characterized by highly desirable viscosity properties.

BACKGROUND OF THE INVENTION

In the past, cough syrups and cough suppressant and sore throat medications have been available as pourable liquids. However, due to the nature of the action of the various active ingredients present in such syrups and medications, it would appear highly desirable to have such products available as gels of increased viscosity to coat the throat and mucous membrane and thereby maintain the active ingredient in more intimate contact with the irritated areas. It is also recognized that it would be highly desirable to provide such a gel product which is easily convertible to a pourable liquid so as to avoid the necessity of producing two separate products, one as a gel and another as a pourable liquid. It is also highly desirable that such an easily convertible product be of the type that it is easily converted from a thixotropic gel to a pourable liquid under normal conditions of use, that is, with moderate hand shaking of the product by the user or by the appropriate amount of shear forces through a dispensing nozzle. Additionally, it is desirable that the thixotropic gel product adequately suspend all the insoluble ingredients in the product and especially the opacifying agent titanium dioxide.

SUMMARY OF THE INVENTION

It has now been found that compositions employing titanium dioxide as an opacifying agent and which are thixotropic gels easily convertible to pourable liquids can be provided according to this invention by employing as the suspending agent Avicel® RC-591 microcrystalline cellulose which is a mixture of about 89 parts microcrystalline cellulose and 11 parts sodium carboxymethylcellulose.

More particularly, aqueous pharmaceutical compositions containing active ingredients and other optional non-active ingredients and employing titanium dioxide as an opacifying agent which are thixotropic gels easily convertible to pourable liquids with moderate hand shaking are provided according to this invention by employing Avicel® RC-591 microcrystalline cellulose as the suspending agent.

DETAILED DESCRIPTION OF THE INVENTION

It has unexpectedly been found that Avicel® RC-591 microcrystalline cellulose provides thixotropic aqueous pharmaceutical compositions containing titanium dioxide as an opacifying agent and easily convertible to pourable liquids upon moderate hand shaking of the product whereas all other suspending agents investigated failed to provide a satisfactory product with such characteristics.

The thixotropic products of this invention are characterized by an initial viscosity at room temperature of from about 6,000 to about 8,000 cps and after hand shaking the product with moderate force for about five seconds (approximately 7 to 10 shakes) the product is converted to a pourable liquid having a viscosity of from about 300 to about 800 cps.

The thixotropic products of this invention comprise from about 1% to about 3% weight/volume of Avicel® RC-591 suspending agent, from about 0.01% to about 0.5% weight/volume titanium dioxide and most preferably about 40% weight/volume of water.

While the vehicle compositions of this invention are especially suitable for use with cough syrups, sore throat and cough suppressant medication formulations, it will be recognized that such vehicle compositions can be employed with any other suitable active ingredient for which one desires to prepare a thixotropic gel formulation which is easily convertible to a pourable liquid. However, the vehicle compositions of this invention are especially useful for providing cough syrup, sore throat and cough suppressant products of such characteristics. Merely as exemplary of the numerous active ingredients that may be employed in the formulations of this invention, there may be mentioned for example, dextromethorphan hydrobromide, guaifenesin, phenylpropanolamine hydrochloride and its other salts, pseudoephedrine hydrochloride and its other salts, chlorpheniramine maleate, doxylamine succinate, acetaminophen, ephedrine sulfate, chlophedianol, codeine sulfate, phenylephrine hydrochloride, diphenhydramine hydrochloride, brompheniramine maleate, phenol, menthol, choline salicylate, sodium salicylate and the like and demulcents such as elm bark, gelatin, glycerin, and pectin and the like.

The suspending agent employed in the compositions of this invention is Avicel® RC-591, which is a commercially available microcrystalline cellulose marketed by FMC Corporation, Food and Pharmaceutical Products Division, Philadelphia, Pa., 19601, and which is said to be a colloidal form of about 89 percent microcrystalline cellulose gel blended with about 11 percent sodium carboxymethylcellulose and dried, and which product is easily dispersed in water. It is insoluble in water, organic solvents and dilute acids. It is partially soluble in dilute alkali. Its chemical and physical specifications are: loss on drying: less than 6 percent at time of shipment; heavy metals: less than 10 parts per million; viscosity of a 1.2 percent solution, 65 ±1 percent; particle size: less than 0.1 percent retained on 60 mesh screen, less than 20 percent retained on a 325 mesh screen. Average particle size is about 28 microns. Its bulk density is about 37 lbs/ft$^3$ loose pack and about 52 lbs/ft$^3$ tight pack. Its specific gravity is 1.55, ash content about 2 percent, pH of a 2 percent dispersion in water is 6 to 8. Said product is described more fully in FMC Corporation bulletin L-318 "Avicel® RC-CL Microcrystalline Cellulose."

While numerous other suspending agents have been tried in order to obtain a product of the characteristics of this invention, none has provided such a product except Avicel® RC-591. Among the numerous other suspending agents tested in an attempt to arrive at a product having the characteristics of the vehicle composition of this invention there may be mentioned, for example, agar, various alginates, carboxymethylcellulose, carboxypolymethylene, carrageenan, colloidal silicon dioxide, corn starch, flowable starch, gelatin, guar gum, hydroxypropylcellulose, hydroxypropyl methylcellulose, maltodextrin, methylcellulose, pectin, polyethylene glycol 8000, polyvinyl alcohol, polyvinylpyrrolidone, tragacanth gum and xanthan gum. Most of these materials did not satisfactorily suspend the titanium dioxide until excessive viscosities were reached and additionally were unable to provide a thixotropic gel formulation that is readily and easily converted to a pourable liquid with only manual shaking of the product with moderate force for about five seconds.

The amount of Avicel® RC-591 suspending agent employed in the compositions of this invention is from about 1% to about 3%, preferably from about 1% to about 2% and most preferably about 1½% weight-/volume based on the total composition. The amount of titanium dioxide opacifying agent employed in the compositions of this invention is from about 0.01% to about 0.5%, preferably from about 0.025% to about 0.1%, preferably about 0.1% weight/volume based on the total composition. While the amount of water in the compositions of this invention can vary over quite a wide range depending upon the total weight and volume of the Avicel® RC-591, titanium dioxide, active ingredients and other optionaL non-active ingredients, generally however, the water content of the composition will range from about 30% to about 60%, preferably about 35% to about 50% and most preferably about 40% weight/volume.

As stated, the compositions of this invention can contain any suitable optional ingredients such as buffers, flavorants, colorants, sweeteners, preservatives, solubilizing agents and the like in amounts generally known for these agents.

The thixotropic vehicle compositions of this invention are characterized by their suitably long shelf-life, by not gelling to an unacceptable extent and by the solids not settling to form a nonuniformly dispersible product. Moreover, the products of this invention soothe sore throats better than any commercially available cough and sore throat preparations and additionally provide improved cough suppression at an earlier time.

Although the vehicle compositions of this invention can be employed with a wide variety of active ingredients to form aqueous pharmaceutical compositions which are thixotropic upon standing but are easily converted to pourable liquids upon shaking with moderate force for about five seconds, the invention will be illustrated by exemplary formulations of the cough and sore throat medication type but it will be appreciated that other formulation for other indications can also be prepared following this invention.

The aqueous vehicle compositions of the invention as easily prepared by adding the suspending agent to water and mixing followed by the addition of the titanium dioxide to the mixture with vigorous mixing.

As exemplary compositions of this invention, there may be mentioned, for example, the following compositions.

Example I
COUGH/SORE THROAT LIQUID FORMULATION

| Ingredients | Amount/30 ml Dose | |
|---|---|---|
| Dextromethorphan HBr | 15.0 | mg |
| Acetaminophen | 650.0 | mg |
| Sugar | 15.3 | g |
| Microcrystalline Cellulose and Sodium CMC (Avicel® RC-591, FMC) | 375.0 | mg |
| Sodium Citrate, Hydrous | 156.6 | mg |
| Citric Acid, Anhydrous | 101.4 | mg |
| Sodium Benzoate | 30.0 | mg |

-continued

| | | |
|---|---|---|
| Sorbitol Solution | 600.0 | mg |
| Glycerin | 600.0 | mg |
| Titanium dioxide | 30.0 | mg |
| Propylene Glycol | 3.6 | g |
| Alcohol, 95% (abs) | 3.0 | ml |
| Flavorant | 10.35 | mg |
| Menthol | 36.0 | mg |
| Colorant | 0.72 | mg |
| Water, Purified, q.s. | 30.0 | ml |

Example II
COUGH/SORE THROAT LIQUID FORMULATION

| Ingredients | Amount/30 ml Dose | |
|---|---|---|
| Dextromethorphan HBr | 10.0 | mg |
| Acetaminophen | 480.0 | mg |
| Sugar | 15.3 | g |
| Microcrystalline Cellulose and Sodium CMC (Avicel® RC-591, FMC) | 375.0 | mg |
| Sodium Citrate, Hydrous | 156.6 | mg |
| Citric Acid, Anhydrous | 101.4 | mg |
| Sodium Benzoate | 30.0 | mg |
| Sodium Saccharin | 12.0 | mg |
| Sorbitol Solution | 600.0 | mg |
| Glycerin | 600.0 | mg |
| Titanium dioxide | 30.0 | mg |
| Propylene Glycol | 4.5 | g |
| Alcohol, 95% (abs) | 2.25 | ml |
| Flavorant | 0.0375 | ml |
| Menthol | 12.0 | mg |
| Colorant | 0.60 | mg |
| Water, Purified, q.s. | 30.0 | ml |

Example III
THROAT COATING COUGH MEDICINE FORMULATION

| Ingredients | Amount/15 ml Dose | |
|---|---|---|
| Dextromethorphan HBr | 30.0 | mg |
| Sugar | 7.65 | g |
| Microcrystalline Cellulose and Sodium CMC (Avicel® RC-591, FMC) | 187.5 | mg |
| Sodium Citrate, Hydrous | 78.3 | mg |
| Citric Acid, Anhydrous | 50.7 | mg |
| Sodium Benzoate | 15.0 | mg |
| Sorbitol Solution | 300.0 | mg |
| Glycerin | 300.0 | mg |
| Titanium dioxide | 15.0 | mg |
| Propylene Glycol | 1.8 | g |
| Alcohol, 95% (abs) | 1.5 | ml |
| Flavorant | 37.5 | μl |
| Menthol | 12.0 | mg |
| Colorant | 3.0 | mg |
| Water, Purified, q.s. | 15.0 | ml |

Example IV
THROAT COATING COUGH MEDICINE FORMULATION

| Ingredients | Amount/15 ml Dose | |
|---|---|---|
| Guaifenesin | 200.0 | mg |
| Sugar | 7.65 | g |
| Microcrystalline Cellulose and Sodium CMC (Avicel® RC-591, FMC) | 187.5 | mg |
| Sodium Citrate, Hydrous | 78.3 | mg |
| Citric Acid, Anhydrous | 50.7 | mg |
| Sodium Benzoate | 15.0 | mg |
| Sorbitol Solution | 300.0 | mg |
| Glycerin | 300.0 | mg |
| Titanium dioxide | 15.0 | mg |
| Propylene Glycol | 1.8 | g |
| Alcohol, 95% (abs) | 1.5 | ml |
| Flavorants | 15.0 | μl |
| Menthol | 12.0 | mg |
| Colorants | 3.75 | mg |
| Water, Purified, q.s. | 15.0 | ml |

Example V
THROAT COATING COUGH MEDICINE FORMULATION

| Ingredients | Amount/15 ml Dose | |
|---|---|---|
| Guaifenesin | 200.0 | mg |
| Phenylpropanolamine HCl | 37.5 | mg |
| Dextromethorphan HBr | 20.0 | mg |

| | -continued | |
|---|---|---|
| Sugar | 7.65 | g |
| Microcrystalline Cellulose and Sodium CMC (Avicel ® RC-591, FMC) | 187.5 | mg |
| Sodium Citrate, Hydrous | 300.0 | mg |
| Citric Acid, Anhydrous | 3.5 | mg |
| Sodium Benzoate | 15.0 | mg |
| Sorbitol Solution | 300.0 | mg |
| Glycerin | 300.0 | mg |
| Titanium dioxide | 15.0 | mg |
| Propylene Glycol | 1.8 | g |
| Alcohol, 95% (abs) | 1.5 | ml |
| Flavorant | 15.0 | μl |
| Menthol | 12.0 | mg |
| Colorants | 1.53 | mg |
| Water, Purified, q.s. | 15.0 | ml |

Example VI
THROAT COATING COUGH MEDICINE FORMULATION

| Ingredients | Amount/15 ml Dose | |
|---|---|---|
| Phenylpropanolamine HCl | 37.5 | mg |
| Dextromethorphan HBr | 20.0 | mg |
| Doxylamine Succinate | 7.5 | mg |
| Sugar | 7.65 | g |
| Microcrystalline Cellulose and Sodium CMC (Avicel ® RC-591, FMC) | 187.5 | mg |
| Sodium Citrate, Hydrous | 300.0 | mg |
| Citric Acid, Anhydrous | 3.5 | mg |
| Sodium Benzoate | 15.0 | mg |
| Sorbitol Solution | 300.0 | mg |
| Glycerin | 300.0 | mg |
| Titanium dioxide | 15.0 | mg |
| Propylene Glycol | 1.8 | g |
| Alcohol, 95% (abs) | 1.5 | ml |
| Flavorant | 37.5 | μl |
| Menthol | 12.0 | mg |
| Colorant | 0.3 | mg |
| Water, Purified, q.s. | 15.0 | ml |

Example VII
THROAT COATING COUGH MEDICINE FORMULATION

| Ingredients | Amount/15 ml Dose | |
|---|---|---|
| Guaifenesin | 200.0 | mg |
| Phenylpropanolamine HCl | 25.0 | mg |
| Dextromethorphan HBr | 20.0 | mg |
| Microcrystalline Cellulose and Sodium CMC (Avicel ® RC-591, FMC) | 187.5 | mg |
| Sodium Citrate, Hydrous | 300.0 | mg |
| Citric Acid, Anhydrous | 3.5 | mg |
| Sodium Benzoate | 15.0 | mg |
| Sorbitol Solution | 300.0 | mg |
| Glycerin | 300.0 | mg |
| Titanium dioxide | 15.0 | mg |
| Propylene Glycol | 2.25 | g |
| Alcohol, 95% (abs) | 1.5 | ml |
| Flavorant | 25.5 | μl |
| Menthol | 18.0 | mg |
| Colorant | 3.0 | mg |
| Sugar | 10.2 | g |
| Water, Purified, q.s. | 15.0 | ml |

Example VIII
THROAT COATING COUGH MEDICINE FORMULATION

| Ingredients | Amount/15 ml Dose | |
|---|---|---|
| Dextromethorphan HBr | 15.0 | mg |
| Doxylamine Succinate | 7.5 | mg |
| Sugar | 7.65 | g |
| Microcrystalline Cellulose and Sodium CMC (Avicel ® RC-591, FMC) | 187.5 | mg |
| Sodium Citrate, Hydrous | 78.3 | mg |
| Citric Acid, Anhydrous | 15.0 | mg |
| Sodium Benzoate | 15.0 | mg |
| Sorbitol Solution | 300.0 | mg |
| Glycerin | 300.0 | mg |
| Titanium dioxide | 15.0 | mg |
| Propylene Glycol | 2.25 | g |
| Alcohol, 95% (abs) | 1.5 | ml |
| Menthol | 11.25 | mg |
| Flavorants | 8.0 | mg |
| Colorant | 0.054 | mg |
| Water, Purified, q.s. | 15.0 | ml |

The unique and highly desirable properties of the compositions of this invention are illustrated by the properties shown in the following table for the composition of the formulation of Example I. After preparation of the composition, the formulation was stored at room temperature and at 45° C. and checked for viscosity and titanium dioxide settling. The viscosity was measured using a Brookfield viscometer, Model LVT, spindle #2 cylindrical, at 25° C., 3 rpm with 100 ml of sample in a 4 fluid ounce bottle. Viscosity values were measured before and after about five seconds of manual shaking of the bottle with moderate force.

TABLE

| Days of Storate at Room Temperature (R.T.) or 45° C. | Viscosity, CPS Before/After Shake | Viscosity Ratio |
|---|---|---|
| 1 at R.T. | 3050/280 | 14/1 |
| 4 at R.T. | 4065/305 | 13/1 |
| 6 at R.T. | 5885/340 | 17/1 |
| 22 at R.T. | 6100/390 | 16/1 |
| 1 at 45° | 6480/355 | 18/1 |
| 4 at 45° | 6655/460 | 15/1 |
| 6 at 45° | 8780/465 | 19/1 |
| 22 at 45° | 7780/470 | 17/1 |

This formulation gave these highly desirable viscosity ratios of viscosity before shake/viscosity after shake while providing an aqueous thixotropic composition on standing which is easily converted to a pourable liquid with moderate shaking and which satisfactorily suspended the titanium dioxide opacifying agent without any undue settling thereof.

I claim:

1. An aqueous vehicle composition comprising water and (a) from about 1% to about 3% weight/volume of a suspendeding agent consisting of about 89% weight microcrystalline cellulose gel blended with about 11 weight percent sodium carboxymethylcellulose, and (b) from about 0.01% to about 0.5% weight/volume titanium dioxide, which composition is a thixotropic gel on standing but is easily convertable to a pourable liquid upon moderate shaking for about five seconds.

2. A composition of claim 1 wherein the suspending agent is present in an amount of from about 1% to about 2% weight/volume and the titanium dioxide is present in an amount of from about 0.025% to about 0.1% weight/volume.

3. A composition of claim 2 wherein the suspending agent is present in an amount of about 1½% weight/volume and the titanium dioxide is present in an amount of about 0.1% weight/volume.

4. A composition of claim 1 having a viscosity upon standing measured at 25° C. of from about 6,000 to about 8,000 cps and, after moderate shaking for about five seconds, a viscosity at 25° C. of from about 300 to about 800 cps.

5. A composition of claim 2 having a viscosity upon standing measured at 25° C. of from about 6,000 to about 8,000 cps and, after moderate shaking for about five seconds, a viscosity at 25° C. of from about 300 to about 800 cps.

6. A composition of claim 3 having a viscosity upon standing measured at 25° C. of from about 6,000 to about 8,000 cps and, after moderate shaking for about five seconds, a viscosity at 25° C. of from about 300 to about 800 cps.

7. A composition of claim 1 which is a cough/sore throat liquid composition.

8. A composition of claim 1 which is a throat coating cough medicine.

9. A composition of claim 1 comprising the following composition.

| Ingredients | Amount/15 ml Dose | |
|---|---|---|
| Dextromethorphan HBr | 15.0 | mg |
| Acetaminophen | 650.0 | mg |
| Sugar | 15.3 | g |
| Microcrystalline Cellulose and Sodium CMC (Avicel ® RC-591, FMC) | 375.0 | mg |
| Sodium Citrate, Hydrous | 156.6 | mg |
| Citric Acid, Anhydrous | 101.4 | mg |
| Sodium Benzoate | 30.0 | mg |
| Sorbitol Solution | 600.0 | mg |
| Glycerine | 600.0 | mg |
| Titanium dioxide | 30.0 | mg |
| Propylene Glycol | 3.6 | g |
| Alcohol, 95% (abs) | 3.0 | ml |
| Flavorant | 10.35 | mg |
| Menthol | 36.0 | mg |
| Colorant | 0.72 | mg |
| Water, Purified, q.s. | 30.0 | ml |

10. A composition of claim 1 comprising the following composition:

| Ingredients | Amount/15 ml Dose | |
|---|---|---|
| Guaifenesin | 200.0 | mg |
| Sugar | 7.65 | g |
| Microcrystalline Cellulose and Sodium CMC (Avicel ® RC-591, FMC) | 187.5 | mg |
| Sodium Citrate, Hydrous | 78.3 | mg |
| Citric Acid, Anhydrous | 50.7 | mg |
| Sodium Benzoate | 15.0 | mg |
| Sorbitol Solution | 300.0 | mg |
| Glycerin | 300.0 | mg |
| Titanium dioxide | 15.0 | mg |
| Propylene Glycol | 1.8 | g |
| Alcohol, 95% (abs) | 1.5 | ml |
| Flavorants | 15.0 | µl |
| Menthol | 12.0 | mg |
| Colorants | 3.75 | mg |
| Water, Purified, q.s. | 15.0 | ml |

11. A composition of claim 1 comprising the following composition:

| Ingredients | Amount/30 ml Dose | |
|---|---|---|
| Dextromethorpham HBr | 10.0 | mg |
| Acetaminophen | 480.0 | mg |
| Sugar | 15.3 | g |
| Microcrystalline Cellulose and Sodium CMC (Avicel ® RC-591, FMC) | 375.0 | mg |
| Sodium Citrate, Hydrous | 156.6 | mg |
| Citric Acid, Anhydrous | 101.4 | mg |
| Sodium Benzoate | 30.0 | mg |
| Sodium Saccharin | 12.0 | mg |
| Sorbitol Solution | 600.0 | mg |
| Glycerin | 600.0 | mg |
| Titanium dioxide | 30.0 | mg |
| Propylene Glycol | 4.5 | g |
| Alcohol, 95% (abs) | 2.25 | ml |
| Flavorant | 0.0375 | ml |
| Menthol | 12.0 | mg |
| Colorant | 0.60 | mg |
| Water, Purified, q.s. | 30.0 | ml |

12. A composition of claim 1 comprising the following composition:

| Ingredients | Amount/15 ml Dose | |
|---|---|---|
| Dextromethorphan HBr | 30.0 | mg |
| Sugar | 7.65 | g |
| Microcrystalline Cellulose and Sodium CMC (Avicel ® RC-591, FMC) | 187.5 | mg |
| Sodium Citrate, Hydrous | 78.3 | mg |
| Citric Acid, Anhydrous | 50.7 | mg |
| Sodium Benzoate | 15.0 | mg |
| Sorbitol Solution | 300.0 | mg |
| Glycerin | 300.0 | mg |
| Titanium dioxide | 15.0 | mg |
| Propylene Glycol | 1.8 | g |
| Alcohol, 95% (abs) | 1.5 | ml |
| Flavorant | 37.5 | µl |
| Menthol | 12.0 | mg |
| Colorant | 3.0 | mg |
| Water, Purified, q.s. | 15.0 | ml |

13. A composition of claim 1 comprising the following composition:

| Ingredients | Amount/15 ml Dose | |
|---|---|---|
| Guaifenesin | 200.0 | mg |
| Phenylpropanolamine HCl | 37.5 | mg |
| Dextromethorphan HBr | 20.0 | mg |
| Sugar | 7.65 | g |
| Microcrystalline Cellulose and Sodium CMC (Avicel ® RC-591, FMC) | 187.5 | mg |
| Sodium Citrate, Hydrous | 300.0 | mg |
| Citric Acid, Anhydrous | 3.5 | mg |
| Sodium Benzoate | 15.0 | mg |
| Sorbitol Solution | 300.0 | mg |
| Glycerin | 300.0 | mg |
| Titanium dioxide | 15.0 | mg |
| Propylene Glycol | 1.8 | g |
| Alcohol, 95% (abs) | 1.5 | ml |
| Flavorant | 15.0 | µl |
| Menthol | 12.0 | mg |
| Colorants | 1.53 | mg |
| Water, Purified, q.s. | 15.0 | ml |

14. A composition of claim 1 comprising the following composition:

| Ingredients | Amount/15 ml Dose | |
|---|---|---|
| Phenylpropanolamine HCl | 37.5 | mg |
| Dextromethorphan HBr | 20.0 | mg |
| Doxylamine Succinate | 7.5 | mg |
| Sugar | 7.65 | g |
| Microcrystalline Cellulose and Sodium CMC (Avicel ® RC-591, FMC) | 187.5 | mg |
| Sodium Citrate, Hydrous | 300.0 | mg |
| Citric Acid, Anhydrous | 3.5 | mg |
| Sodium Benzoate | 15.0 | mg |
| Sorbitol Solution | 300.0 | mg |
| Glycerin | 300.0 | mg |
| Titanium dioxide | 15.0 | mg |
| Propylene Glycol | 1.8 | g |
| Alcohol, 95% (abs) | 1.5 | ml |
| Flavorant | 37.5 | µl |
| Menthol | 12.0 | mg |
| Colorant | 0.3 | mg |
| Water, Purified, q.s. | 15.0 | ml |

15. A composition of claim 1 comprising the following composition:

| Ingredients | Amount/15 ml Dose | |
|---|---|---|
| Dextromethorphan HBr | 15.0 | mg |
| Doxylamine Succinate | 7.5 | mg |
| Sugar | 7.65 | g |
| Microcrystalline Cellulose and Sodium CMC (Avicel ® RC-591, FMC) | 187.5 | mg |

| Ingredients | Amount/15 ml Dose | |
|---|---|---|
| Sodium Citrate, Hydrous | 78.3 | mg |
| Citric Acid, Anhydrous | 15.0 | mg |
| Sodium Benzoate | 15.0 | mg |
| Sorbitol Solution | 300.0 | mg |
| Glycerin | 300.0 | mg |
| Titanium dioxide | 15.0 | mg |
| Propylene Glycol | 2.25 | g |
| Alcohol, 95% (abs) | 1.5 | ml |
| Menthol | 11.25 | mg |
| Flavorants | 8.0 | mg |
| Colorant | 0.054 | mg |
| Water, Purified, q.s. | 15.0 | ml. |

16. A composition of claim 1 comprising the following composition:

| Ingredients | Amount/15 ml Dose | |
|---|---|---|
| Guaifenesin | 200.0 | mg |
| Phenylpropanolamine HCl | 25.0 | mg |
| Dextromethorphan HBr | 20.0 | mg |
| Microcrystalline Cellulose and Sodium CMC (Avicel ® RC-591, FMC) | 187.5 | mg |
| Sodium Citrate, Hydrous | 300.0 | mg |
| Citric Acid, Anhydrous | 3.5 | mg |
| Sodium Benzoate | 15.0 | mg |
| Sorbitol Solution | 300.0 | mg |
| Glycerin | 300.0 | mg |
| Titanium dioxide | 15.0 | mg |
| Propylene Glycol | 2.25 | g |
| Alcohol, 95% (abs) | 1.5 | ml |
| Flavorant | 25.5 | µl |
| Menthol | 18.0 | mg |
| Colorant | 3.0 | mg |
| Sugar | 10.2 | g |
| Water, Purified, q.s. | 15.0 | ml. |

* * * * *